US012690776B2

(12) United States Patent
Wada

(10) Patent No.: US 12,690,776 B2
(45) Date of Patent: Jul. 28, 2026

(54) HEART RATE INFORMATION ACQUISITION SYSTEM, AND BED SYSTEM

(71) Applicant: MINEBEA MITSUMI Inc., Nagano (JP)

(72) Inventor: Satoru Wada, Tama (JP)

(73) Assignee: MINEBEA MITSUMI INC., Nagano (JP)

( * ) Notice: Subject to any disclaimer, the term of this patent is extended or adjusted under 35 U.S.C. 154(b) by 404 days.

(21) Appl. No.: 18/250,823

(22) PCT Filed: Oct. 21, 2021

(86) PCT No.: PCT/JP2021/038930
§ 371 (c)(1),
(2) Date: Aug. 16, 2023

(87) PCT Pub. No.: WO2022/091933
PCT Pub. Date: May 5, 2022

(65) Prior Publication Data
US 2024/0000329 A1 Jan. 4, 2024

(30) Foreign Application Priority Data
Oct. 29, 2020 (JP) ................................. 2020-181871

(51) Int. Cl.
*A61B 5/024* (2006.01)
*A61B 5/00* (2006.01)
(Continued)

(52) U.S. Cl.
CPC ............ *A61B 5/02444* (2013.01); *A61B 5/11* (2013.01); *A61B 5/6892* (2013.01); *A61B 5/113* (2013.01);
(Continued)

(58) Field of Classification Search
None
See application file for complete search history.

(56) References Cited

U.S. PATENT DOCUMENTS

| 7,070,568 B1 * | 7/2006 | Koh ...................... A61N 1/3627 |
| | | 600/529 |
| 10,758,187 B2 * | 9/2020 | Akatsu ................. A61B 5/7235 |
| | (Continued) | |

FOREIGN PATENT DOCUMENTS

| CN | 104994786 A | 10/2015 |
| CN | 109414223 A | 3/2019 |
| | (Continued) | |

OTHER PUBLICATIONS

Clarivate Analytics translation of JP-2000230853-A (Year: 2025).*
(Continued)

*Primary Examiner* — Carl H Layno
*Assistant Examiner* — Manolis Pahakis
(74) *Attorney, Agent, or Firm* — Chrisman Gallo Tochtrop LLC

(57) ABSTRACT

A heartbeat information acquisition system configured to acquire heartbeat information of a subject on a bed, including a plurality of load detectors configured to detect a load of the subject on the bed, a waveform acquisition unit configured to acquire, based on outputs of the plurality of load detectors, a plurality of heartbeat waveforms respectively corresponding to the plurality of load detectors, a waveform selection unit configured to select, from the plurality of heartbeat waveforms, a largest amplitude waveform being a heartbeat waveform having a largest amplitude among the plurality of heartbeat waveforms, and a heartbeat information acquisition unit configured to acquire the heartbeat information of the subject based on an output of a load (Continued)

detector, among the plurality of load detectors, corresponding to the largest amplitude waveform.

11 Claims, 9 Drawing Sheets

(51) Int. Cl.
  *A61B 5/11* (2006.01)
  *A61B 5/113* (2006.01)
(52) U.S. Cl.
  CPC . *A61B 2562/0252* (2013.01); *A61B 2562/046* (2013.01)

(56) References Cited

U.S. PATENT DOCUMENTS

| | | | | |
|---|---|---|---|---|
| 10,888,279 | B2 * | 1/2021 | Akatsu | A61B 5/0816 |
| 11,160,508 | B2 * | 11/2021 | Akatsu | A61B 5/1102 |
| 2005/0039699 | A1 * | 2/2005 | Sato | A01K 1/031 119/712 |
| 2007/0008156 | A1 | 1/2007 | Ueda et al. | |
| 2010/0018327 | A1 | 1/2010 | Kogure et al. | |
| 2010/0049066 | A1 * | 2/2010 | Hatakeyama | A61B 5/347 600/509 |
| 2012/0016247 | A1 | 1/2012 | Vrazic | |
| 2012/0330113 | A1 | 12/2012 | Kogure | |
| 2015/0351693 | A1 | 12/2015 | Berezhyy et al. | |
| 2017/0011261 | A1 * | 1/2017 | Singh | G06V 40/103 |
| 2018/0206793 | A1 * | 7/2018 | Akatsu | A61B 5/0255 |
| 2019/0000350 | A1 * | 1/2019 | Narayan | G16H 50/50 |
| 2019/0076084 | A1 * | 3/2019 | Kanegae | A61B 5/4812 |
| 2019/0150843 | A1 | 5/2019 | Akatsu et al. | |
| 2019/0150844 | A1 | 5/2019 | Akatsu et al. | |
| 2020/0245875 | A1 | 8/2020 | Hayami | |
| 2020/0305798 | A1 | 10/2020 | Ishikawa et al. | |
| 2021/0259562 | A1 * | 8/2021 | Wada | A61B 5/02416 |
| 2021/0338152 | A1 * | 11/2021 | Tätte | A61B 5/0205 |
| 2021/0361239 | A1 * | 11/2021 | Chahine | A61B 5/318 |
| 2021/0398666 | A1 * | 12/2021 | Maslik | A61B 5/4842 |
| 2022/0142582 | A1 | 5/2022 | Masuda | |

FOREIGN PATENT DOCUMENTS

| | | | | | |
|---|---|---|---|---|---|
| CN | 109414224 | A | | 3/2019 | |
| CN | 111050640 | A | | 4/2020 | |
| JP | H04-84938 | A | | 3/1992 | |
| JP | 2000-152917 | A | | 6/2000 | |
| JP | 2000230853 | A | * | 8/2000 | G01L 1/162 |
| JP | 2005-013259 | A | | 1/2005 | |
| JP | 2007-003227 | A | | 1/2007 | |
| JP | 4002905 | B | | 11/2007 | |
| JP | 2011-194050 | A | | 10/2011 | |
| JP | 4829020 | B2 | | 11/2011 | |
| JP | 2016-502888 | A | | 2/2016 | |
| JP | 2017-213123 | A | | 12/2017 | |
| JP | 2018-086284 | A | | 6/2018 | |
| WO | 2017/199597 | A1 | | 11/2017 | |
| WO | 2020/213431 | A1 | | 10/2020 | |

OTHER PUBLICATIONS

Extended European Search Report for corresponding European Application No. 21886052.6 dated Aug. 8, 2024.
Chinese Office Action dated Jul. 13, 2025 for corresponding Chinese Application No. 202180087850.8 and English translation.
International Search Report for corresponding International Application No. PCT/JP2021/038930 mailed Jan. 11, 2022.
Written Opinion for corresponding International Application No. PCT/JP2021/038930 dated Jan. 11, 2022.
Notice of Reasons for Refusal dated Dec. 24, 2024 for corresponding Japanese Application No. 2020-181871 and English translation.

* cited by examiner

HEART RATE INFORMATION ACQUISITION SYSTEM, AND BED SYSTEM

CROSS-REFERENCE TO RELATED APPLICATIONS

This application is a national stage entry of International Application No. PCT/JP2021/038930 filed on Oct. 21, 2021, which claims the benefit of priority to Japanese Application No. JP2020-181871, filed Oct. 29, 2020, the entire disclosures of which are hereby incorporated herein by reference.

TECHNICAL FIELD

The present invention relates to a heartbeat information acquisition system and a bed system.

BACKGROUND ART

In the medical and long-term care fields, detecting the load of a subject on a bed via a load detector and acquiring biological information, such as respiratory rate and heart rate, of the subject based on the detected load has been proposed.

Patent Document 1 discloses a biological information detection device including a plurality of detection units (for example, pressure sensors). The biological information detection device of Patent Document 1 includes a calculation unit calculating, for signals from the plurality of respective detection units, a ratio (signal-to-noise ratio) between an intensity value of a signal based on vibrations of a living body being a detection target and an intensity value of a signal other than the signal based on the vibrations of the living body being the detection target, and a selection unit selecting one or a plurality of the detection units related to a high signal-to-noise ratio. The detection unit selected by the selection unit is used for detecting vibrations due to respiration, heartbeat, body movement, and the like of the living body.

CITATION LIST

Patent Literature

Patent Document 1: JP 2011-194050 A

SUMMARY OF INVENTION

Technical Problem

An object of the present invention is to provide a heartbeat information acquisition system and a bed system capable of acquiring heartbeat information more easily and accurately.

Solution to Problem

According to a first aspect of the present invention, there is provided
a heartbeat information acquisition system configured to acquire heartbeat information of a subject on a bed, the heartbeat information acquisition system including:
a plurality of load detectors configured to detect a load of the subject on the bed;
a waveform acquisition unit configured to acquire, based on outputs of the plurality of load detectors, a plurality of heartbeat waveforms respectively corresponding to the plurality of load detectors;

a waveform selection unit configured to select, from the plurality of heartbeat waveforms, a largest amplitude waveform being a heartbeat waveform having a largest amplitude among the plurality of heartbeat waveforms; and
a heartbeat information acquisition unit configured to acquire the heartbeat information of the subject based on an output of a load detector, among the plurality of load detectors, corresponding to the largest amplitude waveform.

In the heartbeat information acquisition system of the first aspect, the waveform selection unit may obtain an integrated value of amplitude in a predetermined period for each of the plurality of heartbeat waveforms, and select, as the largest amplitude waveform, a waveform having a largest integrated value among the plurality of heartbeat waveforms.

In the heartbeat information acquisition system of the first aspect, the integrated value may be an integrated value of moving average values of each of the plurality of heartbeat waveforms.

In the heartbeat information acquisition system of the first aspect, the waveform selection unit may use only a positive value of the amplitude of each of the plurality of heartbeat waveforms to calculate the integrated value of the amplitude of each of the plurality of heartbeat waveforms.

The heartbeat information acquisition system of the first aspect may further include a body movement determination unit configured to determine whether body movement of the subject is occurring based on an output of at least one of the plurality of load detectors.

In the heartbeat information acquisition system of the first aspect, the waveform selection unit may not select the largest amplitude waveform in a period in which the body movement determination unit determines that the body movement of the subject is occurring.

In the heartbeat information acquisition system of the first aspect, when the body movement determination unit determines that the body movement of the subject is occurring, the waveform selection unit may reselect the largest amplitude waveform after the body movement has stopped.

In the heartbeat information acquisition system of the first aspect, the waveform selection unit may select the largest amplitude waveform in a predetermined period.

In the heartbeat information acquisition system of the first aspect, the heartbeat information acquisition unit may calculate a heart rate of the subject based on autocorrelation of the largest amplitude waveform.

In the heartbeat information acquisition system of the first aspect, the heartbeat information acquisition unit may perform peak detection on the largest amplitude waveform, and calculate a heart rate of the subject based on a detected peak.

In the heartbeat information acquisition system of the first aspect, the heartbeat information acquisition unit may calculate a heart rate of the subject based on frequency analysis of an output of the load detector corresponding to the largest amplitude waveform.

According to a second aspect of the present invention, there is provided a bed system including a bed and the heartbeat information acquisition system according to the first aspect.

Advantageous Effects of Invention

The heartbeat information acquisition system and the bed system according to the present invention can acquire heartbeat information more easily and accurately.

BRIEF DESCRIPTION OF DRAWINGS

FIG. 9(a), FIG. 9(b), FIG. 9(c) and FIG. 9(d) are graphs illustrating how a moving average value over 10 seconds is calculated based on the clipped waveforms illustrated in FIG. 8(a), FIG. 8(b), FIG. 8(c) and FIG. 8(d), respectively.

Figure 10:
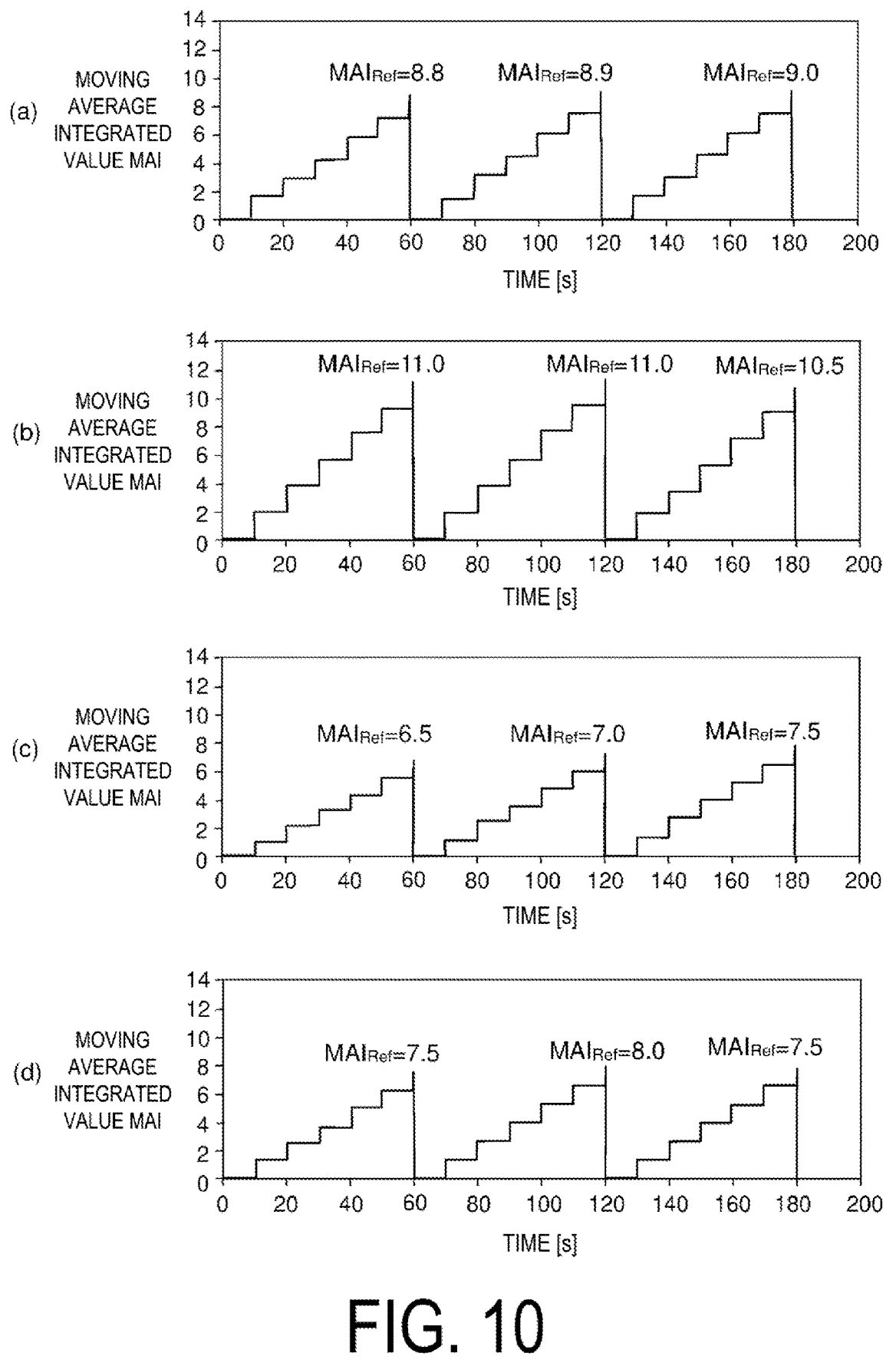

FIG. 10(a), FIG. 10(b), FIG. 10(c), and FIG. 10(d) are graphs illustrating how a moving average integrated value is calculated by integrating a plurality of moving average values including the moving average values illustrated in FIG. 9(a), FIG. 9(b), FIG. 9(c), and FIG. 9(d).

DESCRIPTION OF EMBODIMENTS

Embodiments

A case where a heartbeat information acquisition system 100 (FIG. 1) according to an embodiment of the present invention is used in conjunction with a bed BD (FIG. 2) to calculate (estimate) a heart rate of a subject S on the bed BD will now be described as an example.

Figure 1:
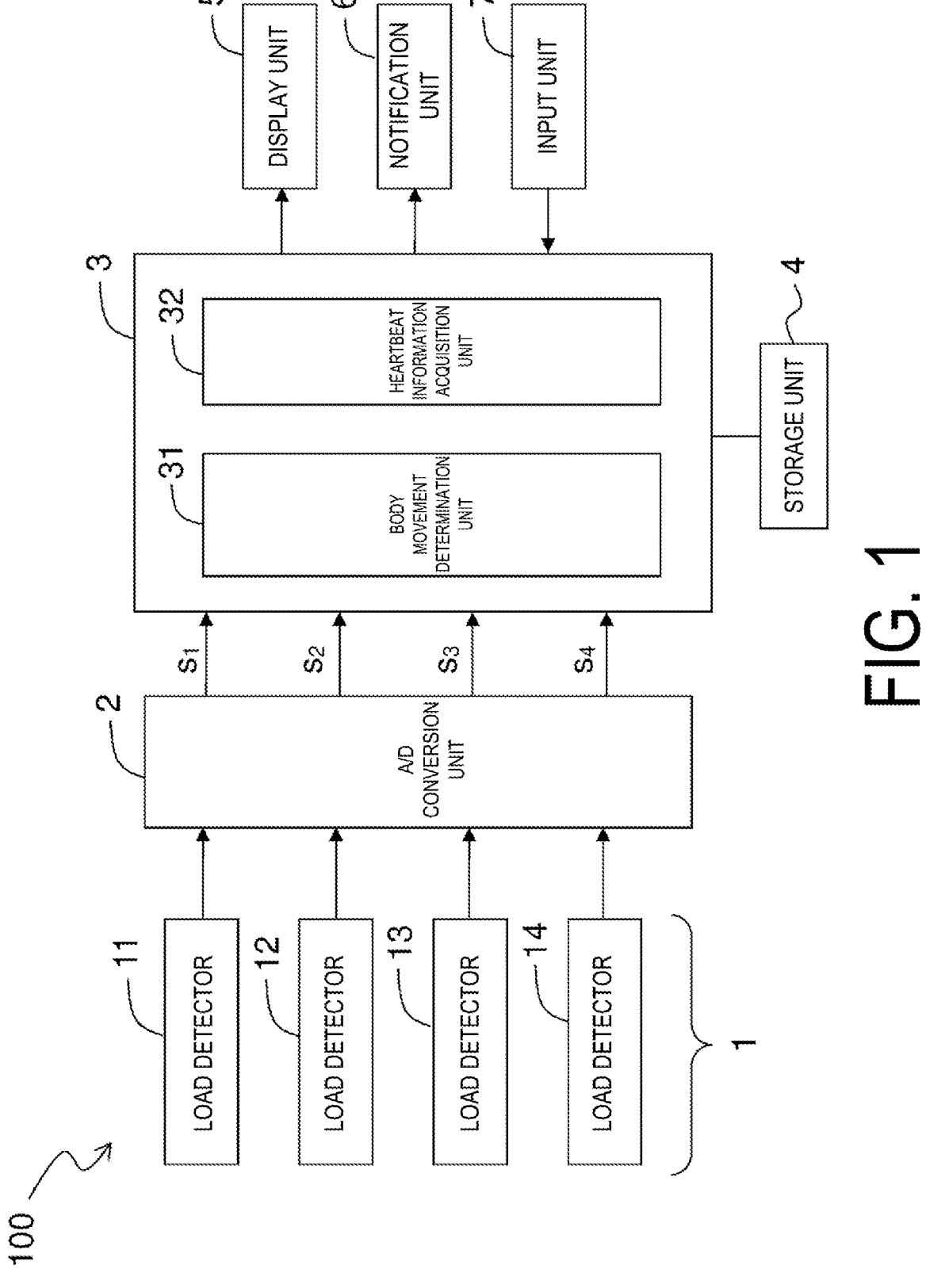
FIG. 1 is a block diagram illustrating a configuration of a heartbeat information acquisition system according to an embodiment of the present invention.

As illustrated in FIG. 1, the heartbeat information acquisition system 100 of the present embodiment primarily includes a load detection unit 1, a control unit 3, and a storage unit 4. The load detection unit 1 and the control unit 3 are connected via an A/D conversion unit 2. A display unit 5, a notification unit 6, and an input unit 7 are further connected to the control unit 3.

The load detection unit 1 includes four load detectors 11, 12, 13, 14. Each of the load detectors 11, 12, 13, 14 is a load detector configured to detect a load using, for example, a beam type load cell. Such a load detector is described in JP 4829020 B and JP 4002905 B, for example. Each of the load detectors 11, 12, 13, 14 is connected to the A/D conversion unit 2 by wiring or wirelessly.

Figure 2:
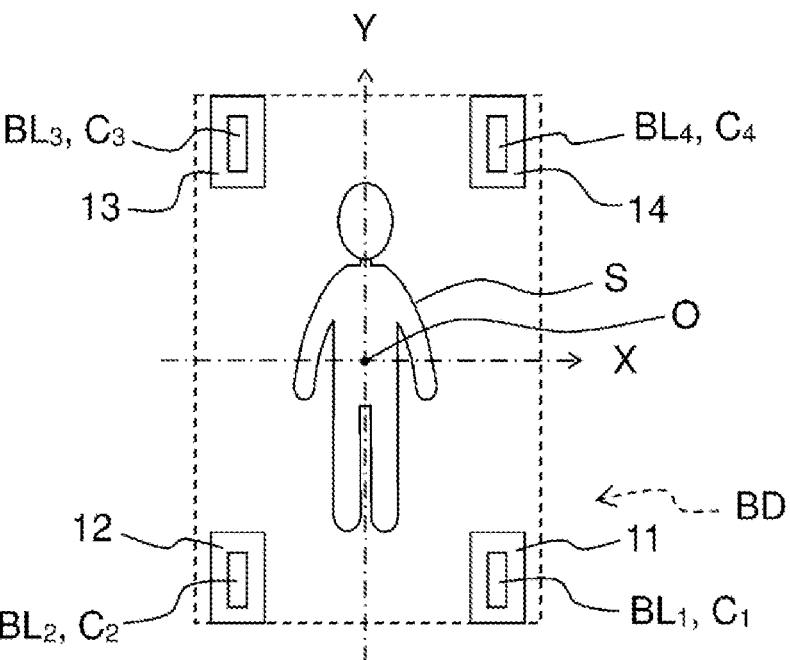
FIG. 2 is an explanatory view illustrating an arrangement of load detectors at a bed.

As illustrated in FIG. 2, the four load detectors 11 to 14 of the load detection unit 1 are respectively disposed below casters $C_1$, $C_2$, $C_3$, $C_4$ attached to lower ends of legs $BL_1$, $BL_2$, $BL_3$, $BL_4$ of the four corners of the bed BD used by the subject S.

The A/D conversion unit 2 includes an A/D converter configured to convert an analog signal from the load detection unit 1 into a digital signal, and is connected to the load detection unit 1 and the control unit 3 by wiring or wirelessly.

The control unit 3 is a dedicated or general-purpose computer, and a body movement determination unit 31 and a heartbeat information acquisition unit 32 are built into an interior of the control unit 3.

The storage unit 4 is a storage device configured to store data used in the heartbeat information acquisition system 100, and a hard disk (magnetic disk), for example, can be used.

The display unit 5 is a monitor, such as a liquid crystal monitor, configured to display information output from the control unit 3 to a user of the heartbeat information acquisition system 100.

The notification unit 6 includes a device, such as a speaker, configured to audibly provide a predetermined notification on the basis of information from the control unit 3.

The input unit 7 is an interface for performing a predetermined input to the control unit 3, and may be a keyboard and a mouse.

An operation of acquiring heartbeat information (heart rate in the present embodiment) of the subject on the bed using such a heartbeat information acquisition system 100 will now be described.

Figure 3:
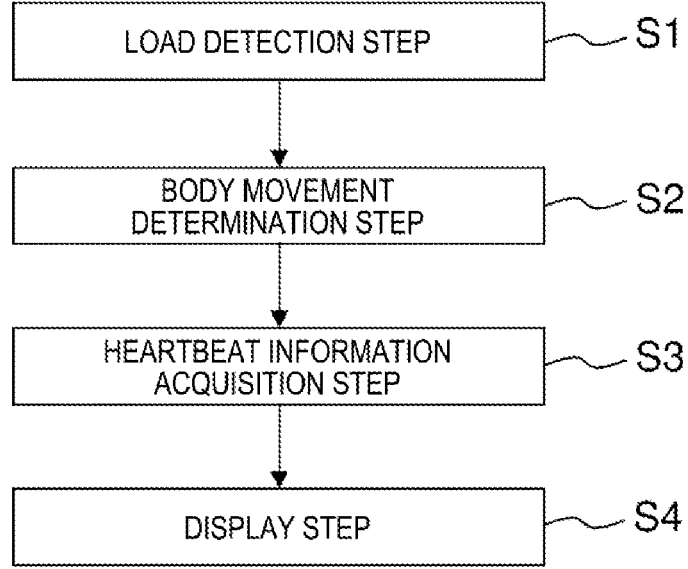
FIG. 3 is a flowchart illustrating a method of acquiring heartbeat information of a subject using the heartbeat information acquisition system.

As illustrated in a flowchart in FIG. 3, the acquisition of the heartbeat information of the subject using the heartbeat information acquisition system 100 includes a load detection step S1, a body movement determination step S2, a heartbeat information acquisition step S3, and a display step S4.

Generally, in the load detection step S1, a load of the subject is detected using the load detectors 11 to 14. In the body movement determination step S2, whether the body movement of the subject has occurred is determined based on the load (load value) detected by at least one of the load detectors 11 to 14. In the heartbeat information acquisition step S3, the heartbeat information of the subject is obtained using the load (load value) detected by the load detectors 11 to 14. In the display step S4, the obtained heartbeat information is displayed on the display unit 5.

Load Detection Step

In the load detection step S1, the load detectors 11, 12, 13, 14 are used to detect the load of the subject S on the bed BD. The load of the subject S on the bed BD is dispersedly applied to and dispersedly detected by the load detectors 11 to 14 disposed below the legs $BL_1$ to $BL_4$ at the four corners of the bed BD.

The load detectors 11 to 14 each detect a load (load change) and output the load as an analog signal to the A/D conversion unit 2. The A/D conversion unit 2 converts the analog signal into a digital signal with a sampling period of, for example, 5 milliseconds, and outputs the digital signal (hereinafter, referred to as a "load signal") to the control unit 3. Hereinafter, the load signals obtained by digitally converting, in the A/D conversion unit 2, the analog signals output from the load detectors 11, 12, 13, 14 are referred to as load signals $s_1$, $s_2$, $s_3$, $s_4$, respectively.

Body Movement Determination Step

In the body movement determination step S2, the body movement determination unit 31 determines whether the body movement of the subject S has occurred by using at least one of the load signals $s_1$ to $s_4$.

This "body movement" means movement of the head, torso (trunk), and four limbs of the subject. The body movement does not include the movement of organs, blood vessels, and the like associated with respiration, heartbeat, and the like. For example, the body movement can be classified into large body movement involving the movement of the torso (trunk) of the subject S and small body movement involving only the movement of the four limbs and the head of the subject. An example of the large body movement is turning over, getting up, or the like, and an example of the small body movement is movement of the limbs, head, or the like during sleep.

The body movement determination unit 31 determines whether the body movement of the subject S has occurred based on the following principle.

Figure 4:
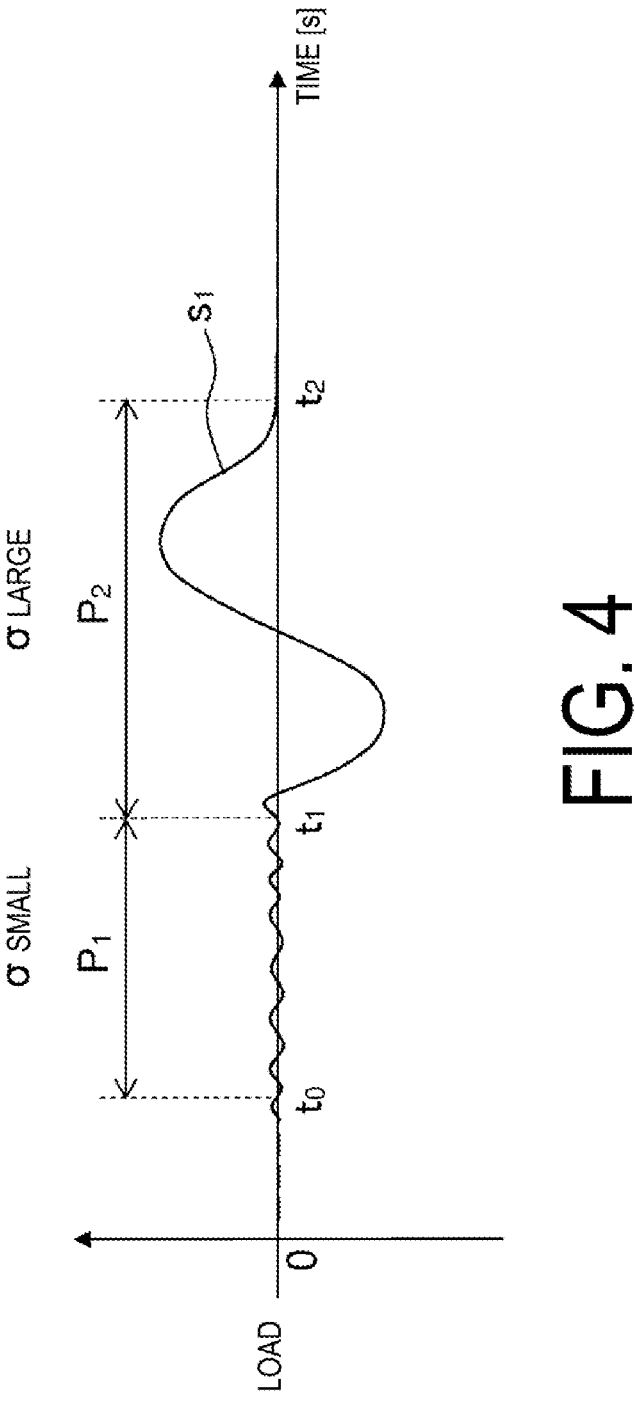
FIG. 4 is a schematic graph illustrating how a load value detected by the load detector fluctuates in both a rest period in which the subject performs only breathing and a body movement period in which the subject performs body movement.

FIG. 4 illustrates a schematic waveform of the load signal $s_1$ from the load detector 11 obtained in a predetermined period including times $t_0$, $t_1$, and $t_2$.

In a period from the time $t_0$ to the time $t_1$ (period $P_1$) in the predetermined period in which the waveform illustrated in FIG. 4 is obtained, no body movement of the subject S is occurring. Thus, the load signal $s_1$ in this period only slightly fluctuates to reflect the movement of the organs and blood vessels of the subject due to the respiration and heartbeat of the subject S, and the amount of the fluctuation is small. In other words, in the period $P_1$ in which no body movement of the subject S is occurring, the fluctuation in a sampling value of the load signal $s_1$ is small.

In a period from the time $t_1$ to the time $t_2$ (period $P_2$) in the predetermined period in which the waveform illustrated in FIG. 4 is obtained, the body movement of the subject S is occurring. Specifically, the subject S is moving the right arm. Thus, the load signal $s_1$ in this period largely fluctuates to reflect the movement of the right arm of the subject S. In other words, in the period $P_2$ in which the body movement of the subject S is occurring, the fluctuation of the sampling value of the load signal $s_1$ is large.

As described above, the fluctuation of the sampling value of the load signal $s_1$ from the load detector 11 is small in the period in which the body movement of the subject S is not occurring, and is large in the period in which the body movement of the subject S is occurring. The same applies to the load signals $s_2$, $s_3$, and $s_4$ from the load detectors 12, 13, and 14.

Thus, the body movement determination unit 31 calculates standard deviation σ representing the magnitude of fluctuation of the sampling value in the predetermined period (five seconds for example) for at least one of load signals $s_1$ to $s_4$ from the load detectors 11 to 14, and determines whether the body movement of the subject S is occurring based on comparison between the calculated standard deviation σ and a predetermined threshold value $σ_{th}$.

Specifically, for example, when the value of the standard deviation σ calculated for a predetermined period is smaller than the predetermined threshold value $σ_{th}$, the body movement of the subject S is determined to be not occurring in that period. On the other hand, for example, when the value of the standard deviation α calculated for a predetermined sampling period is larger than the predetermined threshold value $σ_{th}$, the body movement of the subject S is determined to be occurring in that period. Instead of the standard deviation σ, variance $σ^2$ may be compared with the predetermined threshold value $σ^2_{th}$ to determine whether the body movement of the subject S is occurring.

Heartbeat Information Acquisition Step

In the heartbeat information acquisition step S3, the heartbeat information acquisition unit 32 acquires the heartbeat information of the subject S using the load signals $s_1$ to $s_4$. The heartbeat information is a heart rate in the present embodiment.

Figure 5:
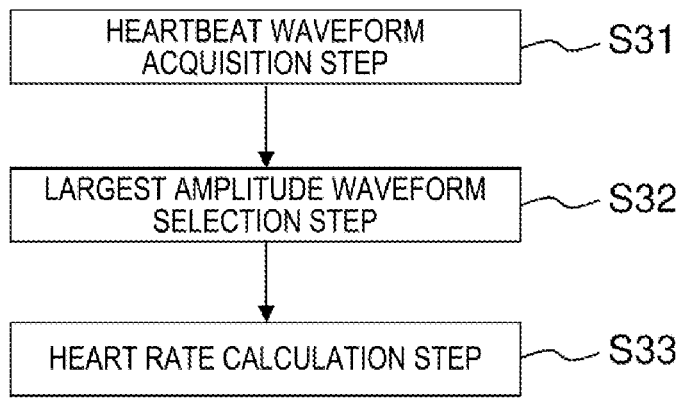
FIG. 5 is a flowchart illustrating a heartbeat information acquisition step in detail.

As illustrated in FIG. 5, the heartbeat information acquisition step S3 includes a heartbeat waveform acquisition step S31, a largest amplitude waveform selection step S32, and a heart rate calculation step S33.

Figure 6:
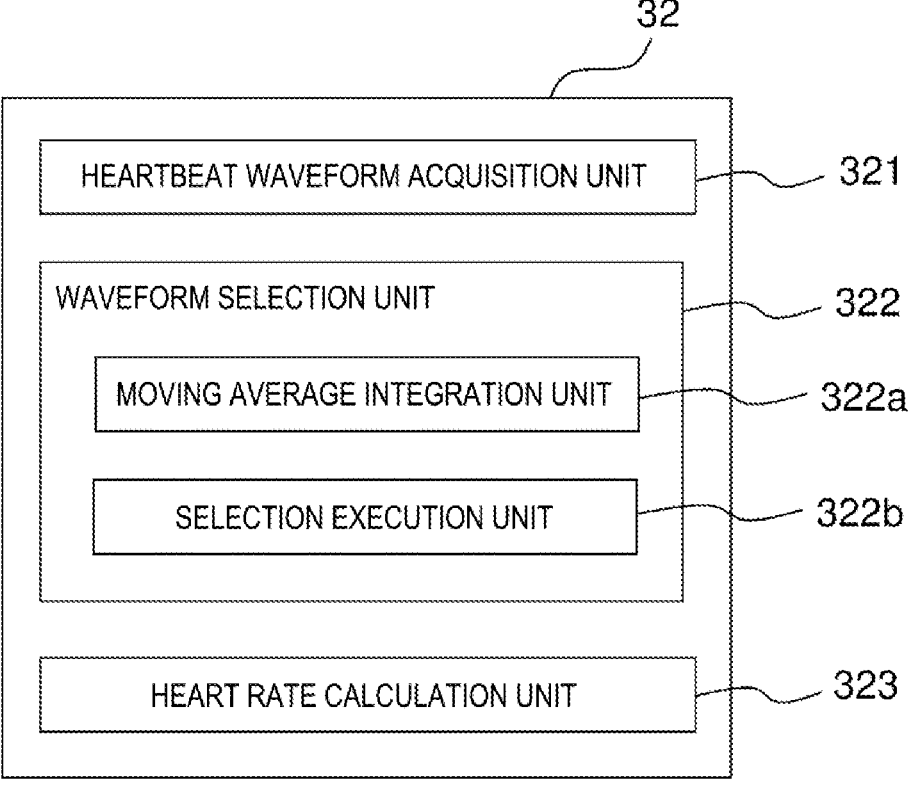
FIG. 6 is a block diagram illustrating a specific configuration of a heartbeat information acquisition unit.
Figure 7:
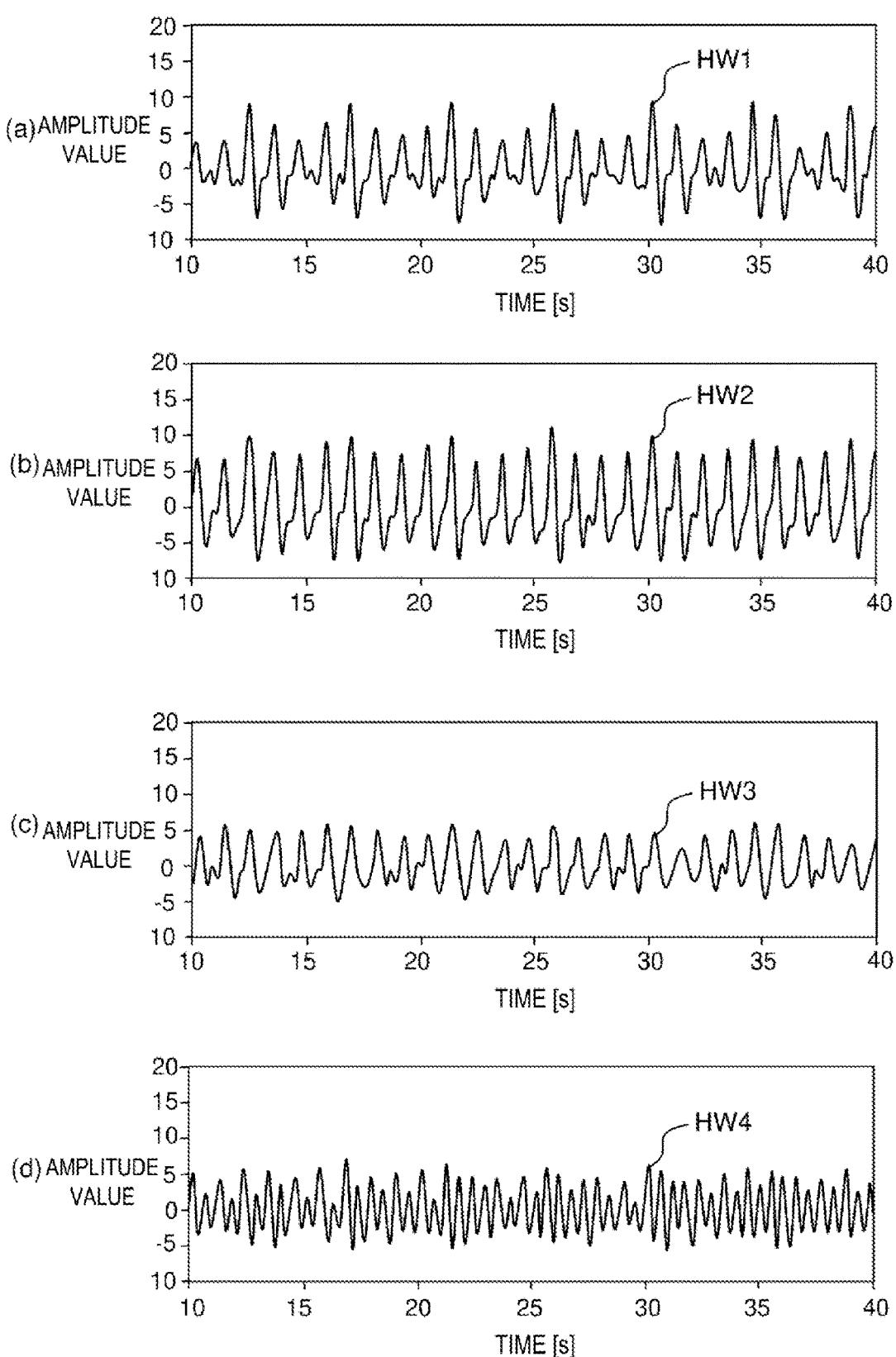
FIG. 7(a), FIG. 7(b), FIG. 7(c), and FIG. 7(d) are graphs illustrating examples of heartbeat waveforms based on outputs from the four load detectors disposed below legs of the bed.
Figure 8:
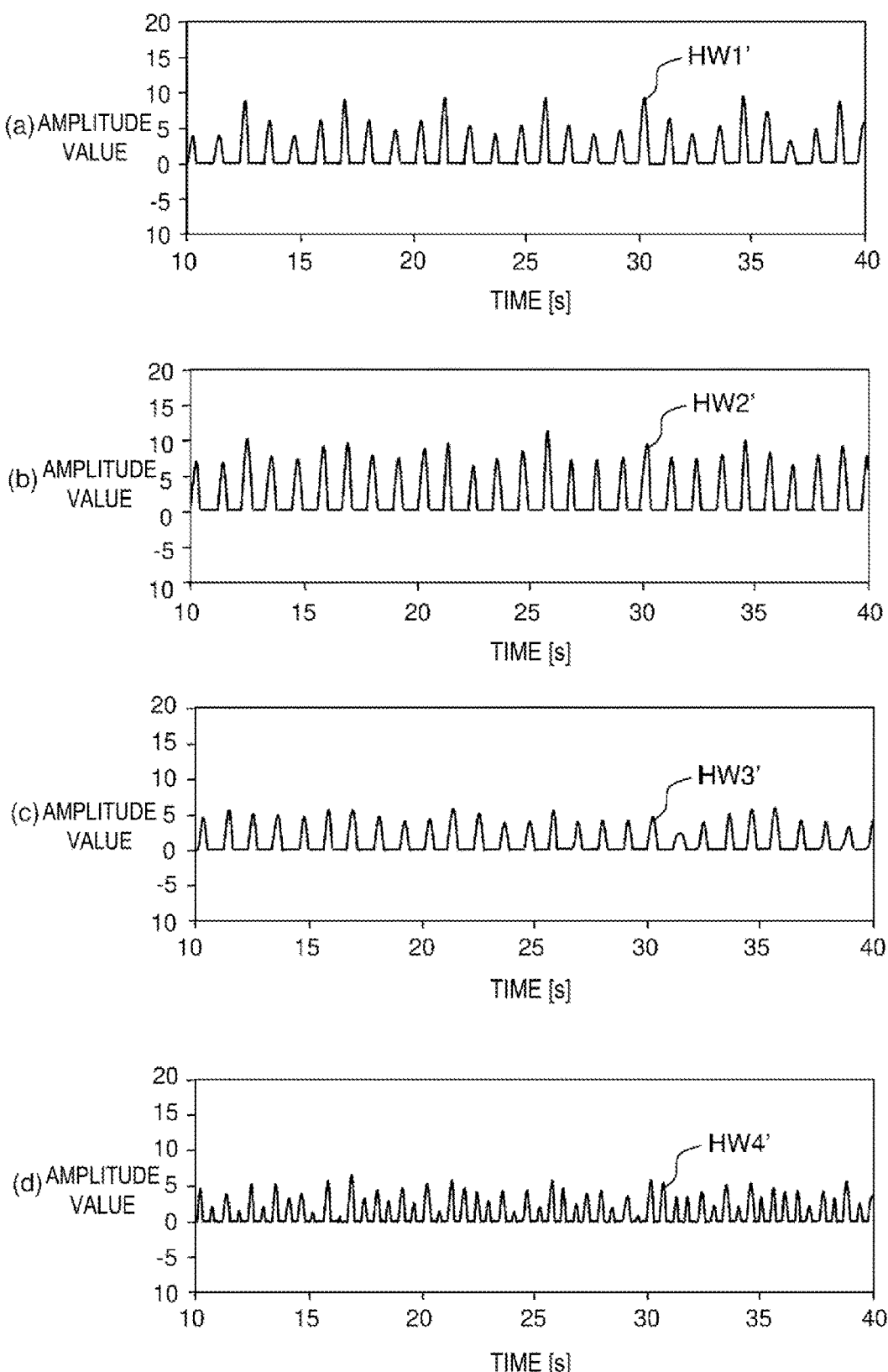
FIG. 8(a), FIG. 8(b), FIG. 8(c) and FIG. 8(d) are graphs illustrating clipped waveforms obtained by performing clipping processing on the heartbeat waveforms illustrated in FIG. 7(a), FIG. 7(b), FIG. 7(c) and FIG. 7(d), respectively.

As illustrated in FIG. 6, the heartbeat information acquisition unit 32 includes a heartbeat waveform acquisition unit 321, a waveform selection unit 322, and a heart rate calculation unit 323. The waveform selection unit 322 includes a moving average integration unit 322a and a selection execution unit 322b.

In the heartbeat waveform acquisition step S31, the heartbeat waveform acquisition unit 321 acquires a heartbeat waveform of the subject S from each of the load signals $s_1$ to $s_4$.

In the present specification and the present invention, "heartbeat waveform" means a waveform indicating a temporal fluctuation of a load value corresponding to the heartbeat of a subject. One period of the heartbeat waveform corresponds to one period of the heartbeat. The amplitude of the heartbeat waveform is correlated with the amount of blood flowing with a single heartbeat. If the other conditions are the same, a larger amount of blood flowing due to the heart beating leads to a heartbeat waveform with a larger amplitude.

Specifically, for example, the heartbeat waveform acquisition unit 321 acquires a heartbeat waveform by the following method.

Since the human heart beats about 30 to 200 times per minute, the frequency of the human heartbeat is about 0.5 to 3.3 Hz (hereinafter, referred to as a "heartbeat band"). Thus, the heartbeat waveform acquisition unit 321 extracts a component having a frequency in the heartbeat band from each of the load signals $s_1$ to $s_4$ using a band-pass filter, and sets the extracted components to be heartbeat waveforms HW1 to HW4.

FIG. 7(a), FIG. 7(b), FIG. 7(c), and FIG. 7(d) respectively illustrate examples of the heartbeat waveforms HW1, HW2, HW3, and HW4 acquired based on the load signals $s_1$, $s_2$, $s_3$, and $s_4$. The heartbeat waveforms HW1 to HW4 illustrated in FIGS. 7(a) to 7(d) are heartbeat waveforms of the subject S in the period from the time 10 s to the time 40 s.

In the largest amplitude waveform selection step S32, the waveform selection unit 322 selects a waveform having the largest amplitude (hereinafter referred to as a "largest amplitude waveform") from the four heartbeat waveforms HW1 to HW4 acquired in the heartbeat waveform acquisition step S31.

Specifically, for example, the waveform selection unit 322 selects the largest amplitude waveform through the following procedure.

(1) Clipping Processing

First, the waveform selection unit 322 causes the moving average integration unit 322a to execute clipping processing of cutting off an amplitude less than zero for each of the heartbeat waveforms HW1 to HW4. The moving average integration unit 322a replaces an amplitude value less than zero with zero for each of the heartbeat waveforms HW1 to HW4.

FIGS. 8(a) to 8(d) respectively illustrate clipped waveforms HW1' to HW4', obtained by the clipping processing on the heartbeat waveforms HW1 to HW4 illustrated in FIGS. 7(a) to 7(d).

(2) Calculation of Moving Average Value MA

Next, the waveform selection unit 322 causes the moving average integration unit 332a to sequentially calculate a moving average value MA of the amplitude of the clipped waveforms HW1' to HW4' for 10 seconds.

Figure 9:
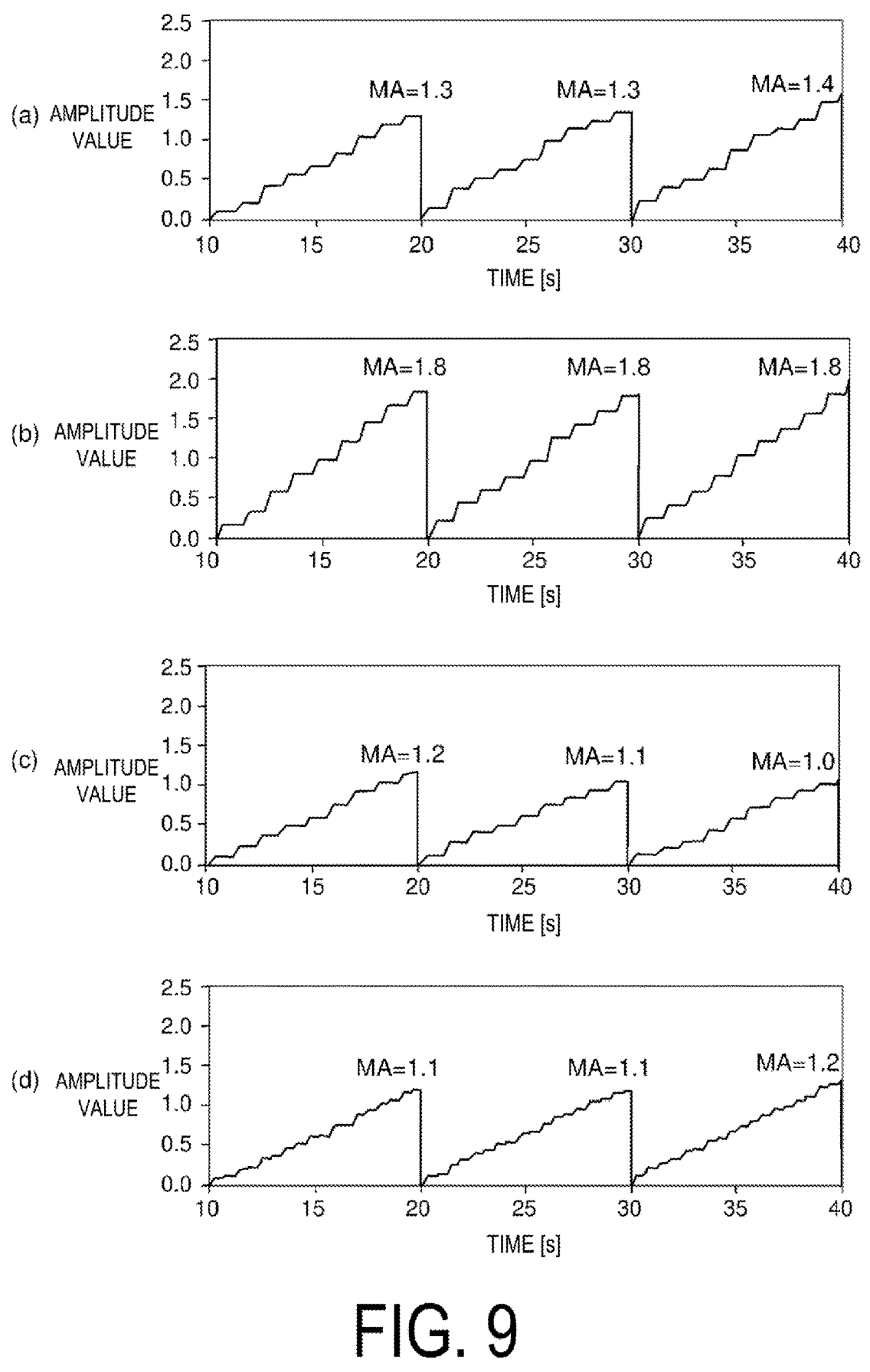

FIG. 9(a) illustrates how the moving average value of the amplitude of the clipped waveform HW1' is sequentially calculated for 10 seconds, based on the clipped waveform HW1' illustrated in FIG. 8(a).

To be more specific, FIG. 9(a) illustrates how the moving average value MA=1.3 is obtained for the period *from* the time 10 s to the time 20 s through a calculation performed with the denominator being "10" and the numerator being the integrated value of the amplitude of the clipped waveform HW1' in that period. FIG. 9(a) also illustrates how the moving average value MA=1.3 is obtained for the period from the time 20 s to the time 30 s and the moving average value MA=1.4 is obtained for the period from the time 30 s to the time 40 s.

FIG. 9(b) illustrates how, through a similar calculation based on the clipped waveform HW2' illustrated in FIG. 8(b), the moving average value MA=1.8 is obtained for the period from the time 10 s to the time 20 s, the moving average value MA=1.8 is obtained for the period from the time 20 s to the time 30 s, and the moving average value MA=1.8 is obtained for the period from the time 30 s to the time 40 s.

FIG. 9(c) illustrates how, through a similar calculation based on the clipped waveform HW3' illustrated in FIG. 8(c), the moving average value MA=1.2 is obtained for the period from the time 10 s to the time 20 s, the moving average value MA=1.1 is obtained for the period from the time 20 s to the time 30 s, and the moving average value MA=1.0 is obtained for the period from the time 30 s to the time 40 s.

FIG. 9(d) illustrates how, through a similar calculation based on the clipped waveform HW4' illustrated in FIG. 8(d), the moving average value MA=1.1 is obtained for the period from the time 10 s to the time 20 s, the moving average value MA=1.1 is obtained for the period from the time 20 s to the time 30 s, and the moving average value MA=1.2 is obtained for the period from the time 30 s to the time 40 s.

(3) Integration of Moving Average Value MA

The waveform selection unit 322 causes the moving average integration unit 332a to sequentially integrate the moving average value MA calculated every 10 seconds to obtain a moving average integrated value MAI. At a point in time when six moving average values MA (60 seconds) are integrated, the moving average integrated value MAI at that point in time is stored as a reference integrated value MAI$_{Ref}$, and the moving average integrated value MAI is reset.

FIGS. 10(a) to 10(d) respectively illustrate how the reference integrated value MAI$_{Re}$f is acquired at a time 60 s, a time 120 s, and a time 180 s, by integrating the moving average value MA calculated every 10 seconds based on the clipped waveforms HW1' to HW4'. The value of the reference integrated value MAI$_{Re}$f thus acquired is as illustrated in each figure.

(4) Selection of Largest Amplitude Waveform

Next, the waveform selection unit 322 causes the selection execution unit 322b to select one of the heartbeat waveforms HW1 to HW4 as the largest amplitude waveform.

Specifically, every 60 seconds, the selection execution unit 322b compares the four reference integrated values MAI$_{Ref}$ based on the respective heartbeat waveforms HW1 to HW4 most currently acquired, and selects the waveform with the largest value of the reference integrated value MAI$_{Ref}$ as the largest amplitude waveform.

In the example illustrated in FIGS. 7 to 10, the value of the reference integrated value MAI$_{Ref}$ based on the heartbeat waveform HW2 is larger than the value of the reference integrated value MAI$_{Ref}$ based on the heartbeat waveforms HW1, HW3, and HW4 at any of the time 60 s, the time 120 s, and the time 180 s. Therefore, the selection execution unit 322b selects the heartbeat waveform HW2 as the largest amplitude waveform immediately after the time 60 s, immediately after the time 120 s, and immediately after the time 180 s.

In the heart rate calculation step S33, the heart rate calculation unit 323 calculates the heart rate of the subject S based on the largest amplitude waveform selected in the largest amplitude waveform selection step S32.

Specifically, for example, the heart rate calculation unit 323 calculates the heart rate of the subject S by the following method.

The heart rate calculation unit 323 calculates an autocorrelation value in the time domain for the heartbeat waveform selected as the largest amplitude waveform from among the heartbeat waveforms HW1 to HW4.

The calculated autocorrelation value indicates the degree of coincidence between the heartbeat waveform and a waveform obtained by shifting the heartbeat waveform by a lag (delay) L in the time axis direction. The degree of coincidence between a waveform and a waveform obtained by shifting the waveform by the lag L in the time axis direction is the highest when the lag L is the same as the period of waveform. Thus, the value of the lag L corresponding to the peak of the autocorrelation value indicates the period of the heartbeat waveform.

Therefore, the heart rate calculation unit 323 detects the peak of the autocorrelation value and determines the lag L corresponding to the peak as the period of the heartbeat waveform.

When there are a plurality of peaks in a range (here, about 0.3 s<L<about 2.0 s) of a range corresponding to the period of the heartbeat, the heart rate calculation unit 323 determines a period T of the heartbeat waveform to be the lag L corresponding to the higher peak.

Then, the heart rate calculation unit 323 calculates a heart rate HR [bpm] by using the following (Equation 1).

[Mathematical Expression 1]

$$HR = 60/T [bpm] \qquad (Equation\ 1)$$

The heartbeat information acquisition unit 32 starts the calculation of the moving average value MA and the moving average integrated value MAI for each of the heartbeat waveforms HW1 to HW4 by the moving average integration unit 322a, at a point in time when "no body movement" is obtained as a result of the body movement determination on the subject S by the body movement determination unit 31 after the heartbeat information acquisition system 100 has been activated. Then, every 60 seconds thereafter, the moving average integration unit 322a calculates the reference integrated value MAI$_{Ref}$ for each of the heartbeat waveforms HW1 to HW4, and the selection execution unit 322b selects the largest amplitude waveform.

Every time a new largest amplitude waveform is selected, the heart rate calculation unit 323 switches to the calculation of the heart rate using the new largest amplitude waveform.

After any one of the heartbeat waveforms HW1 to HW4 has been selected as the largest amplitude waveform at a certain time, the heart rate calculation unit 323 may calculate the heart rate based on the largest amplitude waveform acquired after that time. In this case, the heart rate of the subject S can be more accurately calculated and displayed. Alternatively, after any one of the heartbeat waveforms HW1 to HW4 has been selected as the largest amplitude waveform at a certain time, the heart rate calculation unit 323 may calculate the heart rate based on the heartbeat waveform (that is, the heartbeat waveform involved in the calculation of the reference integrated value $MAI_{Ref}$) before that time. Also in this case, the heart rate of the subject S can be accurately calculated based on the waveform confirmed to be the largest heartbeat waveform through the calculation.

When "body movement occurring" is obtained as a result of the determination by the body movement determination unit 31, in a state of periodically performing the calculation of the reference integrated value $MAI_{Ref}$ and the selection of the largest amplitude waveform (every 60 seconds in the present embodiment), the heartbeat information acquisition unit 32 stops the calculation of the moving average value MA by the moving average integration unit 322a, and resets the moving average integrated value MAI. Furthermore, the selection of the largest selected waveform (designation of any of the heartbeat waveforms HW1 to HW4 as the largest amplitude waveform) is canceled, and the calculation of the heart rate is stopped.

This is because, in a period in which body movement of the subject S is occurring, the heartbeat waveform is affected and disturbed by the body movement, meaning that selection of the largest amplitude waveform and calculation of the heart rate are difficult to perform accurately.

The heartbeat information acquisition unit 32 does not calculate the moving average value MA, the moving average integrated value MAI, and the heart rate in the period in which "body movement occurring" is obtained as a result of the determination by the body movement determination unit 31. In a case where the result of the determination by the body movement determination unit 31 returns to "no body movement" again, the heartbeat information acquisition unit 32 starts again the calculation of the moving average value MA and the moving average integrated value MAI by the moving average integration unit 322a. The moving average integrated value MAI is newly integrated from zero, without using the previous values of the body movement. Then, at a point in time when the reference integrated value $MAI_{Ref}$ is calculated about 60 seconds after the body movement has stopped, the largest amplitude waveform is selected, and the calculation of the heart rate using the selected largest amplitude waveform is resumed.

In many cases, when the position or posture of the subject S on the bed changes due to the body movement of the subject S, the largest amplitude waveform switches to another waveform. Therefore, the largest amplitude waveform is preferably selected again in response to the body movement of the subject S.

Display Step

In the display step S4, the control unit 3 displays the result of the calculation by the heart rate calculation step S33 on the display unit 5. Further, in the display step S4, in addition to or in lieu of the display using the display unit 5, a notification may be made using the notification unit 6. In this case, for example, when the heart rate of the subject S deviates from a predetermined range, a notification sound is generated, notifying a nurse, a caregiver, or the like who is the user of the heartbeat information acquisition system 100 of an abnormal heartbeat state.

The effects of the heartbeat information acquisition system 100 of the present embodiment are summarized below.

The heartbeat information acquisition system 100 of the present embodiment selects the largest amplitude waveform, being a waveform having the largest amplitude, from among the four heartbeat waveforms HW1 to HW4 obtained from the four load detectors 11 to 14, and calculates the heart rate using the selected largest amplitude waveform. With the heart rate thus calculated using a waveform having a large amplitude, the accuracy of the heart rate calculated can be improved.

According to the disclosure of Patent Document 1, a signal having a high signal-to-noise ratio is selected from detection signals of a plurality of detection units to be used for subsequent processing. Unfortunately, even if an output signal used for calculation of a heart rate is selected based on the magnitude of the signal-to-noise ratios of output signals from the load detectors, an appropriate output signal cannot necessarily be selected. This is because with a load detector not largely affected by noise, even a small amplitude of the heartbeat waveform based on the output signal from the load detector leads to a high signal-to-noise ratio.

On the other hand, the heartbeat information acquisition system 100 according to the present embodiment first acquires a heartbeat waveform from the output of the load detector, removes a certain amount of noise, and then selects a waveform to be used for the heart rate calculation by focusing directly on the amplitude of the heartbeat waveform being a main factor affecting the accuracy of heart rate calculation. Thus, the heartbeat waveform appropriate for the heart rate calculation is accurately selected, whereby the heart rate can be calculated with high accuracy.

With the heartbeat information acquisition system 100 of the present embodiment, a load for signal processing required for the waveform selection is smaller than a load in a case where the signal-to-noise ratio is calculated. Such a small signal processing load is particularly advantageous when the heartbeat information acquisition system 100 is implemented as a built-in program of a microcomputer.

The heartbeat information acquisition system 100 according to the present embodiment selects the largest amplitude waveform based on the integrated value of the moving average values of the amplitudes of the heartbeat waveforms HW1 to HW4. With the moving average value of the amplitude thus used, it is possible to suppress the influence of the instantaneous fluctuation (i.e., noise) of the amplitude, whereby the largest amplitude waveform can be more appropriately selected. With the integrated value of the amplitude used, a small difference in the amplitude can be expanded, whereby the largest amplitude waveform can be more appropriately selected.

The heartbeat information acquisition system 100 of the present embodiment includes the body movement determination unit 31, and the heartbeat information acquisition unit 32 stops the selection of the largest amplitude waveform and the calculation of the heart rate in a period in which the body movement determination unit 31 determines that the body movement of the subject is occurring. Thus, the influence of the body movement is suppressed, whereby the largest amplitude waveform is selected and the heart rate is calculated with high reliability.

The heartbeat information acquisition system 100 of the present embodiment reselects the largest amplitude waveform periodically, and when the body movement of the subject S occurs, reselects the largest amplitude waveform after the body movement has stopped. Therefore, highly accurate heart rate calculation can be continued based on the sequentially selected largest amplitude waveform.

Modified Example

In the heartbeat information acquisition system 100 of the above-described embodiment, the following modifications may also be employed.

In the heartbeat information acquisition system 100 of the above-described embodiment, the waveform selection unit 322 selects the largest amplitude waveform based on the calculation of the moving average value MA of the amplitudes of the heartbeat waveforms HW1 to HW4 over 10 seconds, the calculation of the moving average integrated value MAI, and the calculation of the reference integrated value $MAI_{Ref}$ being the integrated value of the moving average values MA over 60 seconds. However, no such limitation is intended.

The period in which the moving average value MA is calculated is not limited to 10 seconds and can be of any duration. The reference integrated value $MAI_{Ref}$ may be an integrated value of the moving average value MA over any period not limited to 60 seconds.

The waveform selection unit 322 may select the heartbeat waveform with the largest moving average value MA in the predetermined period as the largest amplitude waveform, without calculating the moving average integrated value MAI.

The waveform selection unit 322 may select the heartbeat waveform with the largest amplitude integrated value in the predetermined period as the largest amplitude waveform, without calculating the moving average value MA.

The waveform selection unit 322 may select the largest amplitude waveform based on only the magnitude relationship of one amplitude at a predetermined time. The amplitude of the heartbeat waveform can be performed by identifying a peak of the heartbeat waveform by peak detection.

In the heartbeat information acquisition system 100 according to the above-described embodiment, the waveform selection unit 322 performs the clipping processing before calculating the moving average value MA. However, no such limitation is intended.

The clipping processing may not be executed. For example, instead of the clipping processing, a processing of replacing a negative sign of a negative value of the amplitude with a positive sign may be performed. Alternatively, the heartbeat waveform may be shifted by a predetermined amount in the positive direction of the amplitude. According to these processes, the moving average value MA is calculated using only the positive value of the amplitude, whereby the calculation accuracy can be improved.

In the heartbeat information acquisition system 100 according to the above-described embodiment, after the waveform selection unit 322 has selected the largest amplitude waveform, the heart rate is calculated using the selected largest amplitude waveform. However, no such limitation is intended.

For example, the heart rate calculation unit 323 may cause the calculation of the heart rate based on each of the heartbeat waveforms HW1 to HW4 to be performed in advance constantly, and after the waveform selection unit 322 has selected the largest selected waveform, the heart rate calculated in advance based on the selected largest amplitude waveform (that is, any one of the heartbeat waveforms HW1 to HW4) may be displayed on the display unit 5.

In the heartbeat information acquisition system 100 of the above-described embodiment, the heart rate calculation unit 323 calculates the heart rate based on the calculation of the autocorrelation value. However, no such limitation is intended. Various methods may be used to calculate the heart rate based on the heartbeat waveform.

Specifically, for example, peak detection is performed on the largest amplitude waveform, and the period of the largest amplitude waveform is identified based on the distance between peaks. Then, the heart rate HR [bpm] can be calculated by applying the identified period to (Equation 1) described above.

The heart rate calculation unit 323 may perform peak detection on the largest amplitude waveform in a certain period and calculate the heart rate HR [bpm] from the number of peaks.

The heart rate calculation unit 323 may calculate the heart rate of the subject S without using the heartbeat waveform. Specifically, for example, after the largest amplitude waveform is selected, Fourier analysis is performed on the load signal from the load detector corresponding to the largest amplitude waveform to identify the peak frequency appearing in the heartbeat band. Then, the heart rate is calculated with the peak frequency regarded as the heartbeat frequency. Instead of the Fourier analysis, another type of frequency analysis can be used for the heart rate calculation.

In the heartbeat information acquisition system 1000 according to the above-described embodiment, the heartbeat information acquisition unit 32 may include, in addition to the heart rate calculation unit 323 or instead of the heart rate calculation unit 323, a unit acquiring desired heartbeat information such as cardiac output.

The heartbeat information acquisition system 1000 of above-described embodiment does not need to include the body movement determination unit 31.

In the above description, the heartbeat information acquisition system 1000 has been described as an independent system. However, the heartbeat information acquisition system 1000 may be a part of a biological state acquisition (monitoring) system acquiring (monitoring) various types of biological information such as the respiratory rate of a subject.

The heartbeat information acquisition system 100 of the above-described embodiment need not necessarily include all of the load detectors 11 to 14, and may only be provided with any plurality of these. Further, the load detectors need not necessarily be disposed at the four corners of the bed and can be disposed at any position so as to be able to detect the load and fluctuations of the load of the subject on the bed. Further, each of the load detectors 11 to 14 is not limited to being a load sensor that uses a beam type load cell, and, for example, a force sensor can be used.

Figure 11:
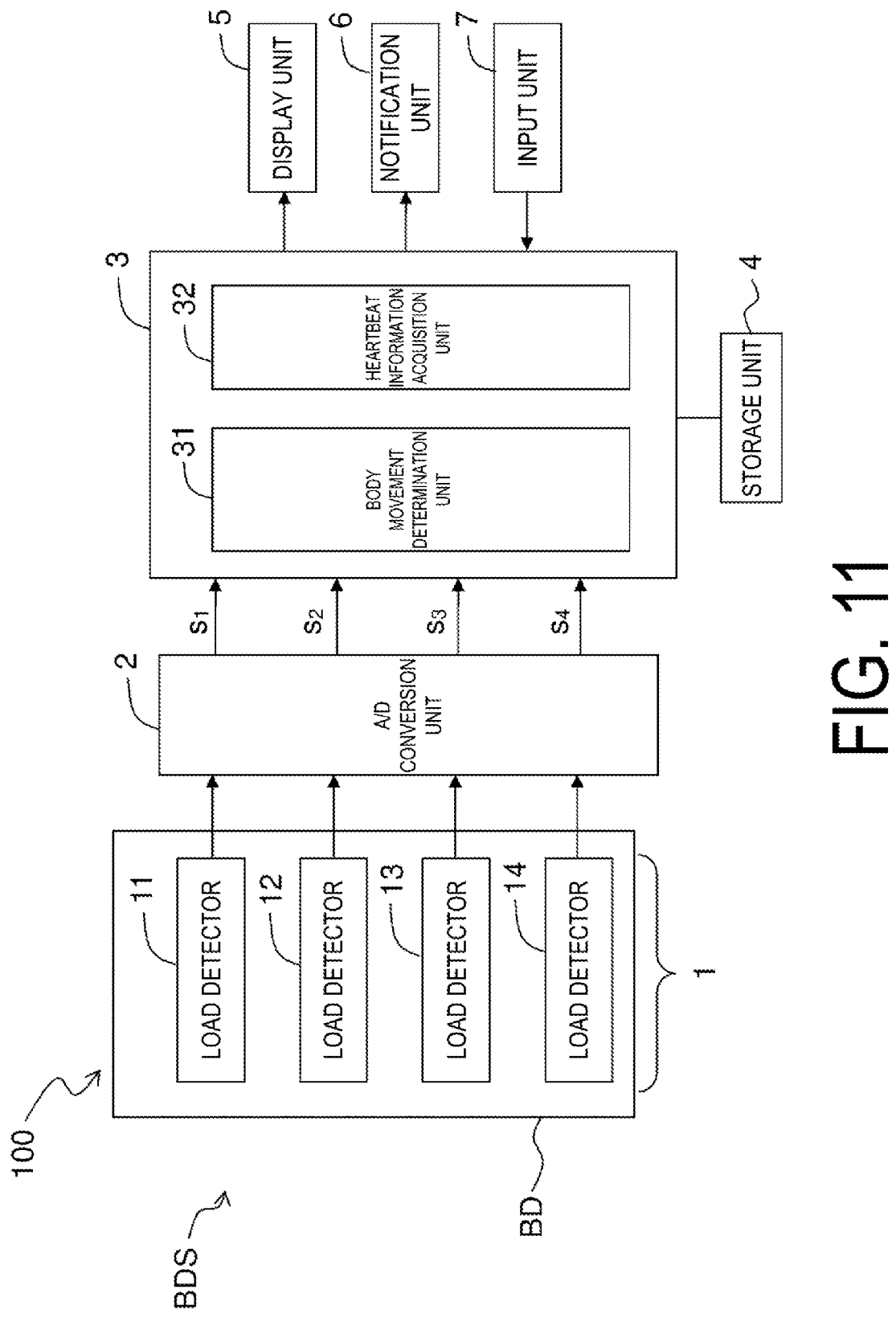
FIG. 11 is a block diagram illustrating an overall configuration of a bed system according to a modified example.

In the heartbeat information acquisition system 100 of the above-described embodiment, each of the load detectors 11 to 14 is disposed below a caster C attached to the lower end of the leg of the bed BD. However, no such limitation is intended. The load detectors 11 to 14 may be respectively provided between the four legs of the bed BD and a bed board of the bed BD or, if the four legs of the bed BD can be vertically separated, may be provided between upper legs and lower legs. Further, the load detectors 11 to 14 may also be integrally or detachably combined with the bed BD to constitute a bed system BDS including the bed BD and the biological information monitoring system 100 of the present embodiment (FIG. 11).

In the heartbeat information acquisition system 100 of the above-described embodiment, a signal amplification unit configured to amplify the load signal from the load detection unit 1, and a filtering unit configured to remove noise from the load signal may be provided between the load detection unit 1 and the A/D conversion unit 2.

In the heartbeat state monitoring system 100 of the above-described embodiment, the display unit 5 may include a simple visual display means, such as a printer for printing and outputting information indicating heartbeat information, a light for displaying heartbeat information, or the like instead of or in addition to the monitor. The notification unit 6 may be provided with a vibration generation unit configured to carry out notification by vibration instead of or in addition to the speaker.

As long as the features of the present invention are maintained, the present invention is not limited to the embodiments described above, and other forms considered within the scope of the technical concept of the present invention are also included within the scope of the present invention.

INDUSTRIAL APPLICABILITY

According to the heartbeat information acquisition system of the present invention, heartbeat information of a subject can be acquired with higher accuracy, making it possible to improve the quality of medical care, long-term care, and the like.

REFERENCE SIGNS LIST

1 Load detection unit, 11, 12, 13, 14 Load detector, 2 A/D conversion unit, 3 Control unit, 31 Body movement determination unit, 32 Heartbeat information acquisition unit, 321 Heartbeat waveform acquisition unit, 322 Waveform selection unit, 322a Moving average integration unit, 322b Selection execution unit, 323 Heart rate calculation unit, 4 Storage unit, 5 Display unit, 6 Notification unit, 7 Input unit, 100 Heartbeat information acquisition system, BD Bed, BDS Bed system

The invention claimed is:

1. A heartbeat information acquisition system configured to acquire heartbeat information of a subject on a bed, the heartbeat information acquisition system comprising:

a plurality of load detectors configured to detect a load of the subject on the bed; and a controller configured to:

acquire, based on outputs of the plurality of load detectors, a plurality of heartbeat waveforms respectively corresponding to the plurality of load detectors;

obtain an integrated value of amplitude in a predetermined period for each of the plurality of heartbeat waveforms;

select, from the plurality of heartbeat waveforms, a waveform having a largest integrated value among the plurality of heartbeat waveforms; and acquire the heartbeat information of the subject based on an output of a load detector, among the plurality of load detectors, corresponding to the waveform having the largest integrated value.

2. The heartbeat information acquisition system according to claim 1, wherein the integrated value is an integrated value of moving average values of each of the plurality of heartbeat waveforms.

3. The heartbeat information acquisition system according to claim 1, wherein the controller is configured to use only a positive value of the amplitude of each of the plurality of heartbeat waveforms to calculate the integrated value of the amplitude of each of the plurality of heartbeat waveforms.

4. The heartbeat information acquisition system according to claim 1, wherein the controller is further configured to determine whether body movement of the subject is occurring based on an output of at least one of the plurality of load detectors.

5. The heartbeat information acquisition system according to claim 4, wherein the controller is configured not to select the waveform having the largest integrated value in a period in which the controller determines that the body movement of the subject is occurring.

6. The heartbeat information acquisition system according to claim 4, wherein when the controller determines that the body movement of the subject is occurring, the controller is configured to reselect the waveform having the largest integrated value after the body movement has stopped.

7. The heartbeat information acquisition system according to claim 1, wherein the controller is configured to select the waveform having the largest integrated value in a predetermined period.

8. The heartbeat information acquisition system according to claim 1, wherein the controller is configured to calculate a heart rate of the subject based on autocorrelation of the waveform having the largest integrated value.

9. The heartbeat information acquisition system according to claim 1, wherein the controller is configured to perform peak detection on the waveform having the largest integrated value, and calculate a heart rate of the subject based on a detected peak.

10. The heartbeat information acquisition system according to claim 1, wherein the controller is configured to calculate a heart rate of the subject based on frequency analysis of an output of the load detector corresponding to the waveform having the largest integrated value.

11. A bed system comprising:

a bed; and the heartbeat information acquisition system according to claim 1.

* * * * *